US006539258B1

(12) United States Patent
Sullivan et al.

(10) Patent No.: US 6,539,258 B1
(45) Date of Patent: Mar. 25, 2003

(54) ENERGY ADJUSTING CIRCUIT FOR PRODUCING AN ULTRA-LOW ENERGY DEFIBRILLATION WAVEFORM WITH FIXED PULSE WIDTH AND FIXED TILT

(75) Inventors: Joseph L. Sullivan, Kirkland, WA (US); Gary Debardi, Kirkland, WA (US); David W. Van Ess, Arlington, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 115 days.

(21) Appl. No.: 09/684,506

(22) Filed: Oct. 6, 2000

(51) Int. Cl.$^7$ .............................. A61N 1/378; A61N 1/39
(52) U.S. Cl. ............................................... 607/7; 607/5
(58) Field of Search ............................. 607/1, 2, 5, 6, 607/7, 8, 10, 143, 145, 148

(56) References Cited

U.S. PATENT DOCUMENTS

| | | |
|---|---|---|
| 3,886,950 A | 6/1975 | Ukkestad et al. |
| 4,559,946 A | 12/1985 | Mower |
| 4,566,457 A | 1/1986 | Stemple |
| 4,628,935 A | 12/1986 | Jones et al. |
| 4,823,796 A * | 4/1989 | Benson ........................ 607/7 |
| 4,850,356 A | 7/1989 | Heath |
| 5,050,601 A | 9/1991 | Kupersmith et al. |
| 5,107,834 A | 4/1992 | Ideker et al. |
| 5,111,813 A | 5/1992 | Charbonnier et al. |
| 5,312,442 A | 5/1994 | O'Phelan |
| 5,372,606 A | 12/1994 | Lang et al. |
| 5,425,749 A | 6/1995 | Adams |
| 5,439,482 A | 8/1995 | Adams et al. |
| 5,441,520 A | 8/1995 | Olsen et al. |
| 5,447,519 A | 9/1995 | Peterson |
| 5,456,690 A | 10/1995 | Duong-Van |
| 5,489,293 A | 2/1996 | Pless et al. |
| 5,531,765 A | 7/1996 | Pless |
| 5,562,710 A | 10/1996 | Olsen et al. |
| 5,593,427 A | 1/1997 | Gliner et al. |
| 5,601,612 A | 2/1997 | Gliner et al. |
| 5,607,454 A | 3/1997 | Cameron et al. |
| 5,620,469 A | 4/1997 | Kroll |
| 5,632,267 A | 5/1997 | Högnelid et al. |

(List continued on next page.)

OTHER PUBLICATIONS

Morgan, Carlton B. et al., "Energy Attenuation for Pediatric Application of AEDs," *AHA Scientific Conference on VF: A Pediatric Problem*, P4, Jul. 9, 1998, (Poster Presentations—Abstracts).

*Primary Examiner*—Willis R. Wolfe
(74) *Attorney, Agent, or Firm*—Christensen O'Connor Johnson Kindness PLLC (57) ABSTRACT

An energy adjusting circuit for use with a defibrillator. The energy adjusting circuit reduces the defibrillation pulse energy that would otherwise be applied to the patient by the defibrillator. The energy adjusting circuit can be part of the defibrillator itself, or part of an adapter coupled to the output ports of a conventional defibrillator. In an adapter designed for pediatric defibrillation, the adapter may include paddles configured for use on babies and small children. The energy adjusting circuit may be formed entirely from passive components and may include a divider circuit with two resistors. The resistance of the two resistors is selected so as to absorb a predetermined percentage of the defibrillation pulse energy that would otherwise be applied to the patient. An isolation circuit may be further included to assist with the measurement of ECG signals through the electrodes. The components of the energy adjusting circuit can be selected so as to produce a defibrillation waveform that has a desired pulse width and tilt, both of which are approximately fixed over an expected range of patient impedances. The defibrillator may be configured to recognize the presence of the energy adjusting circuit, and to indicate to the user that the energy selection ranges have been adjusted accordingly.

36 Claims, 4 Drawing Sheets

U.S. PATENT DOCUMENTS

| | | |
|---|---|---|
| 5,662,687 A | 9/1997 | Hedberg et al. |
| 5,674,253 A | 10/1997 | Adams et al. |
| 5,713,924 A | 2/1998 | Min et al. |
| 5,713,927 A | 2/1998 | Hampele et al. |
| 5,722,994 A | 3/1998 | Norén et al. |
| 5,735,879 A | 4/1998 | Gliner et al. |
| 5,836,978 A * | 11/1998 | Giliner et al. ......... 607/7 |
| 5,999,852 A | 12/1999 | Elabbady et al. |
| 6,047,212 A * | 4/2000 | Giliner et al. ......... 607/7 |
| 6,101,413 A * | 8/2000 | Olson et al. ......... 607/5 |
| 6,125,298 A * | 9/2000 | Olson et al. ......... 607/5 |
| 6,134,468 A * | 10/2000 | Morgan et al. ......... 607/5 |
| 6,370,428 B1 * | 4/2002 | Synder et al. ......... 607/5 |
| 6,374,137 B1 * | 4/2002 | Morgan et al. ......... 607/5 |

\* cited by examiner

ENERGY ADJUSTING CIRCUIT FOR PRODUCING AN ULTRA-LOW ENERGY DEFIBRILLATION WAVEFORM WITH FIXED PULSE WIDTH AND FIXED TILT

FIELD OF THE INVENTION

The invention relates generally to defibrillators and, more particularly, to an apparatus for adjusting the energy of a defibrillation pulse.

BACKGROUND OF THE INVENTION

One of the most common and life-threatening medical conditions is ventricular fibrillation, a condition where the human heart is unable to pump the volume of blood required by the human body. The generally accepted technique for restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a switching mechanism is closed, the stored energy is transferred to a patient in the form of a large current pulse. The current pulse is applied to the patient via a pair of electrodes positioned on the patient's chest. While most contemporary external defibrillators have applied monophasic waveforms to patients, biphasic waveforms are now being used more frequently due to research that indicates that a biphasic waveform may limit the resulting heart trauma associated with the defibrillation pulse.

The American Heart Association has recommended a range of energy levels for the first three defibrillation pulses applied by an external defibrillator. The recommended energy levels are: 200 joules for a first defibrillation pulse; 200 or 300 joules for a second defibrillation pulse; and 360 joules for a third defibrillation pulse, all within a recommended variance range of no more than plus or minus 15 percent according to standards promulgated by the Association for the Advancement of Medical Instrumentation (AAMI). These high energy defibrillation pulses are required to ensure that a sufficient amount of the defibrillation pulse energy reaches the heart of the patient and is not dissipated in the chest wall of the patient.

High energy defibrillation pulses in these ranges are generally designed for certain types of defibrillation in adults. While most external defibrillators are designed to provide defibrillation pulses at these energy levels, other applications may require lower energy defibrillation pulses. For example, low energy defibrillation pulses may be required when defibrillating babies or small children, or when internal paddles are coupled to the defibrillator for use in surgery to directly defibrillate the heart, or for cardioversion of some arrhythmias in both pediatrics and adults.

With regard to babies and small children, the AHA guidelines call for energy settings of 2 joules per kilogram for neonatal defibrillation and 0.5 joules per kilogram for synchronous cardioversion with an Edmark waveform. Designing an external defibrillator so as to be able to provide these low energy levels that are required for babies, as well as the normal high energy levels that are required for adults, increases the complexity and cost of an external defibrillator. Accordingly, there is a need for a simplified, cost-effective design for an external defibrillator that can provide low energy defibrillation pulses appropriate for children, as well as the normal energy defibrillation pulses for adults.

Another consideration with regard to the energy levels of defibrillation pulses is in regard to varying patient impedance levels. More specifically, when a defibrillating pulse is applied to a patient, the pulse encounters a resistance to the flow of electrical current through the patient. The resistance of a patient's thorax to the flow of electrical current is called transthoracic impedance (TTI). The magnitude of current flowing through a patient is directly proportional to the magnitude of the voltage difference across the electrodes used to deliver the defibrillation pulse to the patient and inversely proportional to the patient's TTI.

External defibrillators are likely to encounter patients with a wide range of TTI values. Thus, one challenge that is faced by external defibrillator manufacturers is to design defibrillators that work well over a wide range of patient TTI values. With regard to defibrillators that are designed to apply pulses to adults, while such conventional defibrillators are often specified for and tested with 50 ohm loads, adult patient TTI can vary greatly in a range from 25 to 180 ohms. Average adult patient TTI in a hospital setting is about 80 ohms. Children's TTIs can also vary over wide ranges.

Defibrillator circuits which generate damped sine and truncated exponential pulses respond differently to variations in transthoracic impedance. Damped sine defibrillator impedance response is passive; that is, the response is determined entirely by the amount of capacitance, inductance, and resistance in the circuit. As impedance increases, defibrillating pulse duration increases and peak current decreases.

Several factors affect the shape of waveforms produced by truncated exponential defibrillators in response to different TTI values. Both the capacitance and resistance of the circuit determine passively how quickly the current drops after its initial peak. The active control of a switch that truncates the discharge determines the duration of each phase of the pulse. By design, pulse duration typically increases with increasing TTI values. This is done to allow additional time for energy delivery before the pulse is truncated.

Prior art defibrillators that are designed for adult defibrillation are calibrated for energy delivery at a single, specified load impedance, typically 50 ohms. However, as noted earlier, the TTI of many adult patients exceeds 50 ohms. As a result, the amount of energy actually delivered to a patient is different than the energy level selected by the operator. With damped sine waveforms, patients with TTI greater than 50 ohms receive higher energy than the energy level selected by the operator. With truncated exponential waveforms having fixed durations, patients with TTI greater than 50 ohms receive less energy than the selected energy level. The peak current delivered to patients also drops as patient TTI increases. Prior art defibrillators using truncated exponential waveforms typically adjust the duration of the waveforms (i.e., increased duration with increased impedance) to compensate for a decrease in energy delivered. However, partly because of a reduction in peak current produced in higher impedance patients, long duration truncated exponential waveforms may be less effective among high impedance patients. See, for example, the article "Transthoracic Defibrillation of Swine with Monophasic and Biphasic Waveforms," Circulation 1995, Vol. 92, p. 1634, in which the authors Gliner et al. acknowledge that, for a biphasic truncated exponential waveform, pulse durations exceeding 20 milliseconds are less effective.

Recognizing that patient TTI values affect the amount of current actually delivered to a patient, the prior art has proposed various techniques designed to compensate for varying patient impedance values. A number of these prior art techniques are discussed in commonly assigned U.S. Pat. No. 5,999,852, to Elabbady et al., which is hereby incorporated by reference. Elabbady et al. also discuss a method by which the patient's TTI is used to control the amount of energy contained in a defibrillation pulse that is applied to the patient.

Such prior art external defibrillators are typically designed to provide shocks with a waveform having either a fixed pulse width or a fixed tilt or droop. If the pulse width is fixed, then the tilt would vary inversely with patient impedance. Conversely, if the tilt is fixed, then the pulse width would vary according to patient impedance. Thus, these conventional external defibrillators require additional circuitry that enables the defibrillator to adjust the shock waveform so as to achieve the selected amount of energy in the given waveform, based on the patient impedance. This additional circuitry tends to increase the complexity and cost of the external defibrillator. Accordingly, there is a need for a simplified, cost-effective design for an external defibrillator that can provide a waveform with a relatively fixed pulse width and tilt over an expected range of patient impedances.

The present invention is directed to providing an apparatus that overcomes the foregoing and other disadvantages. More specifically, the present invention is directed to an energy adjusting circuit for a defibrillator that produces a low energy defibrillation waveform with a fixed pulse width and fixed tilt.

SUMMARY OF THE INVENTION

In accordance with the present invention, an energy adjusting circuit is provided for a defibrillator. The energy adjusting circuit adjusts the defibrillation pulse energy that would otherwise be applied to the patient. The energy adjusting circuit can be part of the defibrillator itself, or part of an adapter coupled to the output ports of a conventional defibrillator. In an adapter embodiment, the adapter can optionally have paddles configured for use on small patients such as babies and small children, so as to avoid confusion with the regular defibrillation paddles that are otherwise connected to the defibrillator.

In accordance with another aspect of the invention, the energy adjusting circuit comprises a divider circuit. The divider circuit is used to dissipate a predetermined portion of the shock energy so that a predetermined low energy pulse is delivered to the patient. In one particular embodiment, two resistors are connected to form an energy divider, with the paddles being connected across one of the resistors. The resistance ratio of the two resistors is predetermined so that a predetermined percentage of the defibrillation pulse energy is provided to the patient. In particular, the resistance values are predetermined so that in conjunction with the patient impedance, the external defibrillator scales the full energy shock in the predetermined ratio so as to deliver a shock with the desired energy level.

In accordance with yet another aspect of the invention, in an embodiment where two resistors are connected to form an energy divider, an isolation network may be connected in series with the second resistor. The paddles may then be connected across the series connection of the isolation network and second resistor. The isolation network helps allow ECG signals to be monitored via the therapy electrodes/paddles. As another embodiment, the first resistor may be divided into two resistors, one of each being placed in series with each of the two connections back to the defibrillation energy and control circuitry. The dividing of the first resistor into two separate resistors helps mitigate the effect of the series resistance of the first resistor.

In accordance with still another aspect of the invention, the external defibrillator can be configured to recognize that the adapter is present and to scale the displayed energy level settings. For example, the external defibrillator may have energy settings ranging from 2 joules to 360 joules and the adapter may have a 10:1 energy reduction ratio. With this feature, the external defibrillator would recognize the presence of the adapter and would display or in some manner indicate that the energy settings range from 0.2 joules to 36 joules.

In accordance with yet another aspect of the invention, the divider circuit reduces the effect of patient impedance on the equivalent impedance of the "network" formed by the divider circuit and the patient impedance. Thus, different patient impedances will not significantly affect the tilt of the waveform. By optimizing this effect, the external defibrillator, in effect, delivers shocks having a fixed pulse width and a fixed tilt. As a result, the need for adjusting the waveform based on patient impedance is significantly reduced or even eliminated.

In accordance with a further aspect of the invention, the external defibrillator can be configured to deliver a waveform with an optimal pulse width and tilt. For example, the defibrillator can be configured to generate a waveform with the pulse width and tilt designed to maximize successful treatment, or reduce the size of the storage capacitor or some other parameter.

In accordance with yet another aspect of the invention, the external defibrillator can be configured to have a single charge level (i.e., the energy storage capacitor is always recharged to the same predetermined level) but provide variable energy level shocks through the use of one or more energy adjusting circuits.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
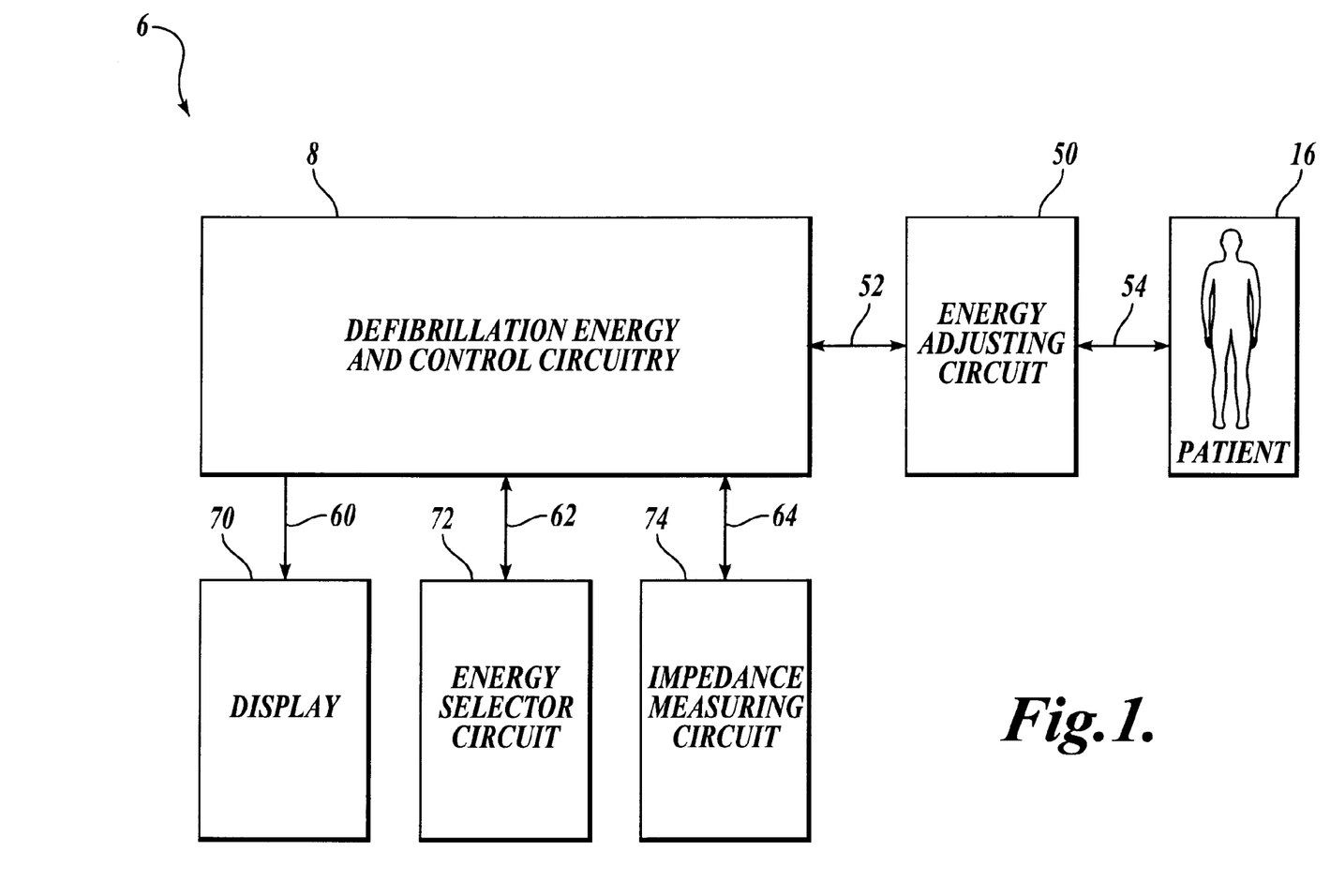
FIG. 1 is a block diagram of a defibrillator coupled to a patient through an energy adjusting circuit that is formed in accordance with the present invention.

FIG. 1 is a block diagram illustrating the components of a defibrillator 6 with an energy adjusting circuit 50 formed in accordance with the present invention. The defibrillator 6 includes defibrillation energy and control circuitry 8 which is coupled through a line 52 to an energy adjusting circuit 50 which is coupled through a line 54 to a patient 16. As will be described in more detail below, the lines 52 and 54 and the other lines discussed herein may consist of multiple lines. The defibrillation energy and control circuitry 8 generates and applies defibrillation pulses through the line 52, which in accordance with the present invention have their levels adjusted by the energy adjusting circuit 50 before being applied to the patient 16 through line 54.

As will be discussed in more detail below with reference to FIG. 6, the defibrillation energy and control circuitry 8 typically includes an energy storage capacitor on which a high energy electric charge is accumulated. Also typically included is a switching mechanism, which when closed, transfers the stored energy from the capacitor in the form of a large current pulse. The current pulse is applied to the patient 16 via a pair of electrodes positioned on the patient's chest (i.e., line 54). The switching mechanism used in most contemporary external defibrillators is a high energy transfer relay. A discharge control signal causes the relay to complete an electrical circuit between the storage capacitor and a waveshaping circuit whose output is connected to the electrodes attached to the patient. As will also be discussed in more detail below with reference to FIG. 6, the switching mechanisms in the defibrillation energy and control circuitry 8 may be designed to apply monophasic or multiphasic defibrillation pulses to the patient 16.

A display 70 is coupled through a line 60 to the defibrillation energy and control circuitry 8. The display 70 provides information to a user regarding the defibrillator operation. An energy selector circuit 72 is coupled through a line 62 to the defibrillation energy and control circuitry 8. The energy selector circuit 72 supplies energy setting information to the defibrillation energy and control circuitry 8 and instructs the defibrillator regarding the defibrillation pulse energy to be delivered to the patient 16. The energy selector circuit 72 may include a continuous dial, which allows a user to select an energy level from a set number of discrete energy levels, such as 100 joules, 200 joules, 300 joules, and 360 joules, for example. In an embodiment where the defibrillator is automated with preprogrammed energy levels, the continuous dial selector may not be present.

An impedance measuring circuit 74 is coupled through a line 64 to the defibrillation energy and control circuitry 8. The defibrillator may utilize the impedance measuring circuitry 74 to measure the impedance of the patient 16 through the line 54 (which as described in more detail below may consist of two electrodes) before delivering a defibrillation pulse. The impedance measuring circuit 74 may use any of the known transthoracic impedance measuring techniques, including a high frequency, low level current pulse technique, a sensing resistance technique, or a low intensity sensing shock technique. Of these, a high frequency, low level current technique may be preferable for impedance measurement outside of delivering a defibrillation pulse. In general, the impedance measurements and resulting operation of the defibrillator are described more detail in the previously noted U.S. Pat. No. 5,999,852, to Elabbady et al., which was previously incorporated herein by reference.

As will be described in more detail below, in the preferred embodiment the energy adjusting circuit 50 is used to dissipate a predetermined portion of the defibrillation pulse energy so that a predetermined low energy pulse is delivered to the patient 16. The energy adjusting circuit 50 can be part of the defibrillator itself, or part of an adapter coupled to the output port of a conventional defibrillator.

As previously described, low energy defibrillation pulses may be required when, for example, special paddles are coupled to the defibrillator for pediatric defibrillation, or for use in surgery to directly defibrillate the heart, or for cardioversion of some arrhythmias in both pediatrics and adults. In a preferred embodiment for pediatric applications, the energy adjusting circuit 50 may be formed as an adapter which includes special paddles configured for use on small patients such as babies and small children. Attaching neonatal type paddles to the energy adjusting circuit 50 may help avoid potential confusion for a user who might not otherwise realize that they are utilizing an energy adjusting circuit adapter. However, the adapter could also be designed to allow attachments of other electrode types.

The energy adjusting circuit 50 may be designed with a set or variable energy reducing capabilities. As an example, in a set embodiment, the energy adjusting circuit 50 may be designed with a 10:1 energy reducing ratio, such that only 10% of the defibrillation energy is delivered to the patient. In a preferred embodiment, the defibrillator 6 can be configured to recognize that the energy adjusting circuit 50 is present and to scale the energy level settings appropriately. In one example, the defibrillator has energy settings ranging from 2 joules to 360 joules, and the energy adjusting circuit 50 is designed with a 10:1 reduction ratio. In this embodiment, the defibrillator would be able to detect the presence of the energy adjusting circuit 50, and would provide an indication, such as on the display 70 or through a gauge on the energy selector circuit 72, that the potential energy settings range from 0.2 joules to 36 joules.

The utilization of the energy adjusting circuit 50 in an Edmark defibrillator is relatively straightforward, but additional considerations arise when utilizing the energy adjusting circuit 50 in a typical biphasic defibrillator. Modern biphasic defibrillators typically adjust the delivered energy waveform based on the patient impedance (e.g., as measured through a circuit such as impedance measuring circuit 74). Thus, if the energy adjusting circuit 50 is attached to the defibrillator output, then the defibrillator will adjust its waveform based on the energy adjusting circuit's impedance rather than the patient impedance, particularly if the energy adjusting circuit's impedance is significantly greater than the patient's impedance. However, consideration of the principles involved reveals that this approach is consistent with the goal of the biphasic defibrillator's intended waveform adjustment.

The ultimate goal of the biphasic truncated exponential waveform adjustment is to produce the maximum voltage across the heart cell membrane, as is well-known in the art. The adjustment is necessary because the tilt (droop) in the applied waveform varies from one patient to the next (due to variances in the patient's impedance). However, when the energy adjusting circuit 50 is coupled into the circuit, the waveform will droop approximately the same amount regardless of the patient impedance (assuming that the energy adjusting circuit's impedance is a significantly greater factor than the impedance of the patient). Therefore, very little or no adjustment is required for the waveform. As a result, a waveform can be produced with an approximately fixed pulse width and a fixed tilt (droop), over an expected range of patient impedances.

Prior art defibrillators have been designed with a fixed pulse width or a fixed tilt, but not both. In the past, if the pulse width was fixed, then the tilt would vary according to the patient impedance. Alternatively, if the tilt was fixed then the pulse width would need to vary. In some embodiments, both the tilt and pulse width were made to vary. Again, in the present invention, the effects of these variables are reduced or even effectively eliminated through the use of the energy adjusting circuit 50. In other words, when the energy adjusting circuit 50 is used, the patient impedance is not a major factor in determining the defibrillation wave shape, which allows for. an optimal pulse width and tilt combination to be selected. A specific example of a selection of a specific pulse width and tilt will be described in more detail below with reference to FIG. 6.

Figure 2:
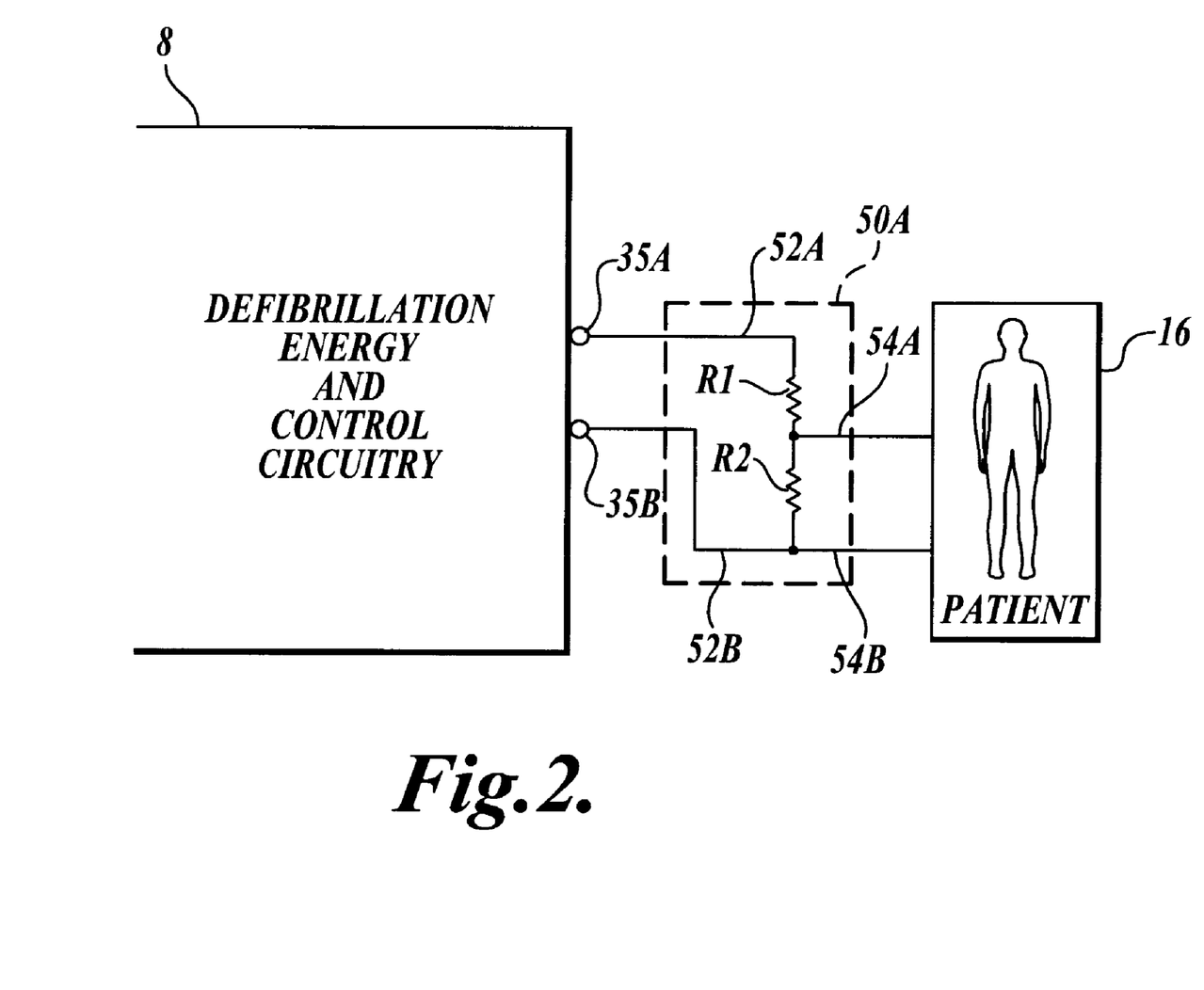
FIG. 2 is a schematic diagram of a first embodiment of the energy adjusting circuit of FIG. 1.

A first embodiment of the energy adjusting circuit 50 is shown in FIG. 2. As shown in FIG. 2, the energy adjusting circuit 50A includes a divider circuit formed with two resistors R1 and R2. The divider circuit is used to dissipate a predetermined portion of the defibrillation pulse energy so that a predetermined low energy pulse is delivered to the patient 16. The energy adjusting circuit 50A is coupled to the defibrillation energy and control circuitry 8 through two output ports 35A and 35B. More specifically, resistor R1 is coupled to the output port 35A by a coupler 52A, while resistor R2 is coupled to the output port 35B by a coupler 52B. The energy adjusting circuit 50A is coupled to the patient 16 through two electrodes and paddles, 54A and 54B. The first electrode 54A is coupled to the circuit node between the resistors R1 and R2. The second electrode 54B is coupled to the other end of the resistor R2 and the output port 35B.

As noted above, the impedance of the energy adjusting circuit 50 can be designed to reduce the defibrillation pulse energy by a selected level. For example, where a 10:1 reduction ratio is desired, the values of resistors R1 and R2 are selected so as to absorb most of the defibrillation pulse energy, with only allowing 10% of the energy to be applied to the patient 16. In one embodiment, practical values for the resistors R1 and R2 are in the range from 5–100 ohms.

As illustrated in FIG. 2, the resistor R1 is in series with the circuit path between the output ports 35A and 35B, and the resistor R2 is in parallel with the patient 16. Thus, assuming the impedance of resistor R1 is significantly greater than that of the patient 16, the resistor R1 will absorb most of the defibrillation pulse energy. The resistor R2 being in parallel with the patient 16, will absorb a portion of the energy in accordance with the current that flows through it rather than through the patient 16. The voltage drop across the resistor R2 and the patient 16 will be approximately the same, given that they are in parallel.

Figure 3:
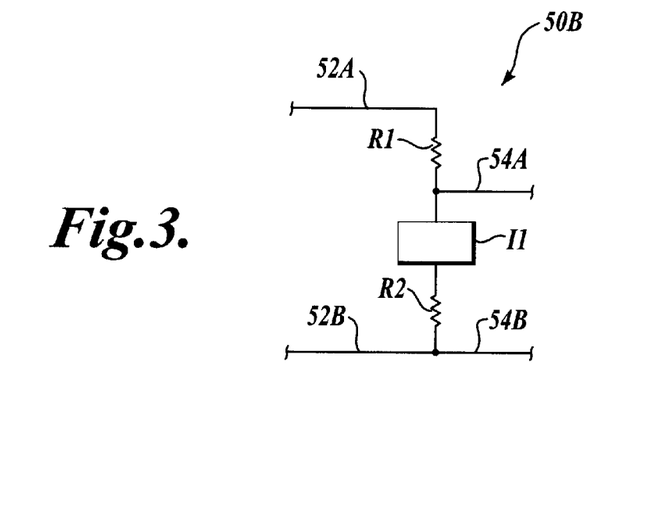
FIG. 3 is a schematic diagram of a second embodiment of the energy adjusting circuit of FIG. 1.

FIG. 3 shows a second embodiment of the energy adjusting circuit 50. The energy adjusting circuit 50B of FIG. 3 is somewhat similar to the energy adjusting circuit 50A of FIG. 2. Thus, the energy adjusting circuit 50B also includes a divider circuit formed of the two resistors R1 and R2. However, the energy adjusting circuit 50B also includes an isolation network I1 coupled in series with the resistor R2. Thus, the isolation network I1 and the resistor R2 are coupled in series between the first electrode 54A and the second electrode 54B.

The energy adjusting circuit 50B of FIG. 3 is designed to assist with the monitoring of ECG signals via the therapy electrodes. In other words, with regard to the energy adjusting circuit 50A of FIG. 2, in an embodiment where the resistors R1 and R2 are given values in the range from 5–100 ohms, the resistors may interfere with the ECG signal. ECG monitors typically must have a shunt impedance of at least 500K ohms (AAMI requires about 1.2M ohms for ECG monitors) even with the large defibrillation electrodes. Thus, the energy adjusting circuit 50A is most useful in an embodiment using separate ECG monitoring electrodes, while the energy adjusting circuit 50B of FIG. 3 is more useful to allow the ECG signals to be monitored via the therapy electrodes as is a common practice.

The isolation network I1 of FIG. 3 is designed to pass the large defibrillation signals but block the low level ECG signals. Thus, the isolation network I1 is used to isolate the shunt resistance R2 from the ECG signals. The series resistance of R1 (e.g., which may be about 40 ohms in one embodiment) is not significant when compared to the source impedance of the electrode which typically ranges from 1,000–50,000 ohms.

Figure 4:
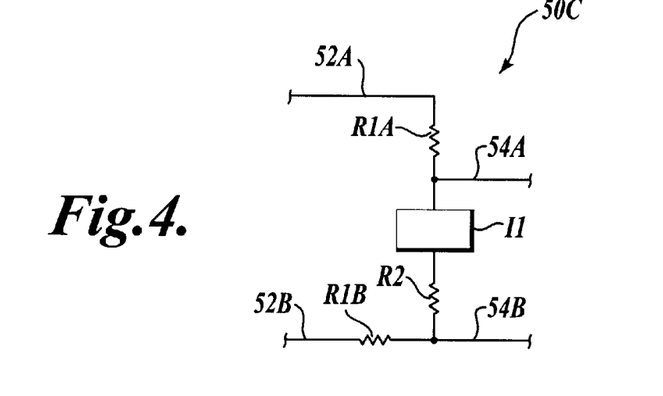
FIG. 4 is a schematic diagram of a third embodiment of the energy adjusting circuit of FIG. 1.

As illustrated in FIG. 4, the small effect of the resistor R1 can be mitigated by dividing the resistor R1 into two resistors of a value of approximately half of the original resistor, and putting one of the resistors in each leg of the attenuator. As shown in FIG. 4, in the energy adjusting circuit 50C, the resistor R1 has been divided into two resistors R1A and R1B. The resistor R1A is coupled between the coupler 52A and the electrode 54A, while the resistor R1B is coupled between the coupler 52B and the electrode 54B. As noted above, the resistors R1A and R1B may be each approximately half the value of the original resistor R1 (in one embodiment making them approximately 20 ohms apiece).

Figure 5:
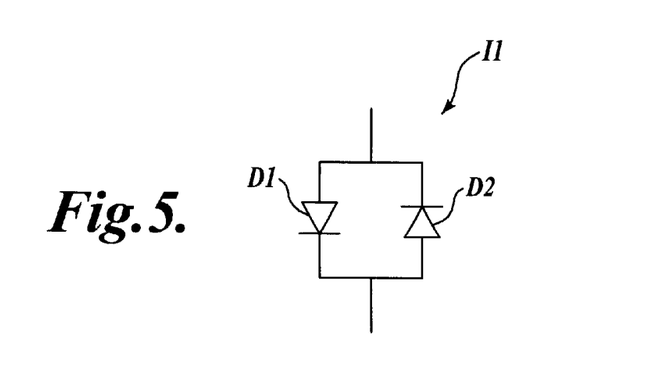
FIG. 5 is a schematic diagram of an embodiment of the isolation network of FIGS. 3 and 4.

FIG. 5 shows an embodiment of the isolation network I1 of FIGS. 3 and 4. It is noted that the isolation network may be implemented in many ways, and that FIG. 5 merely shows one example. In the example of FIG. 5, the isolation network utilizes the nonlinear impedance of two semiconductor diodes D1 and D2 to block low level signals while passing large level signals. The diodes D1 and D2 may be selected to provide the desired transition to high impedance at about 400 millivolts. If a higher or lower transition is desired, either different diode ratings or series combinations of diodes may be used. While FIG. 5 is illustrated using diodes, it is understood that any component which can handle the high currents and which has a nonlinear transfer function can be used in this design. As illustrated in FIG. 5, the diodes D1 and D2 are coupled such that the anode of diode D1 is coupled to the cathode of diode D2, while the cathode of diode D1 is coupled to the anode of diode D2.

It is noted that a particular advantage of the energy adjusting circuits shown in FIGS. 2–5 is the relatively simple design and passive nature of the components. This design avoids the need for certain types of relatively expensive and more complicated switching components (e.g., switched attenuators). Thus, FIGS. 2–5 provide a simplified, cost effective design for an external defibrillator that can provide low energy defibrillation pulses appropriate for children, as well as the normal energy defibrillation pulses for adults.

Figure 6:
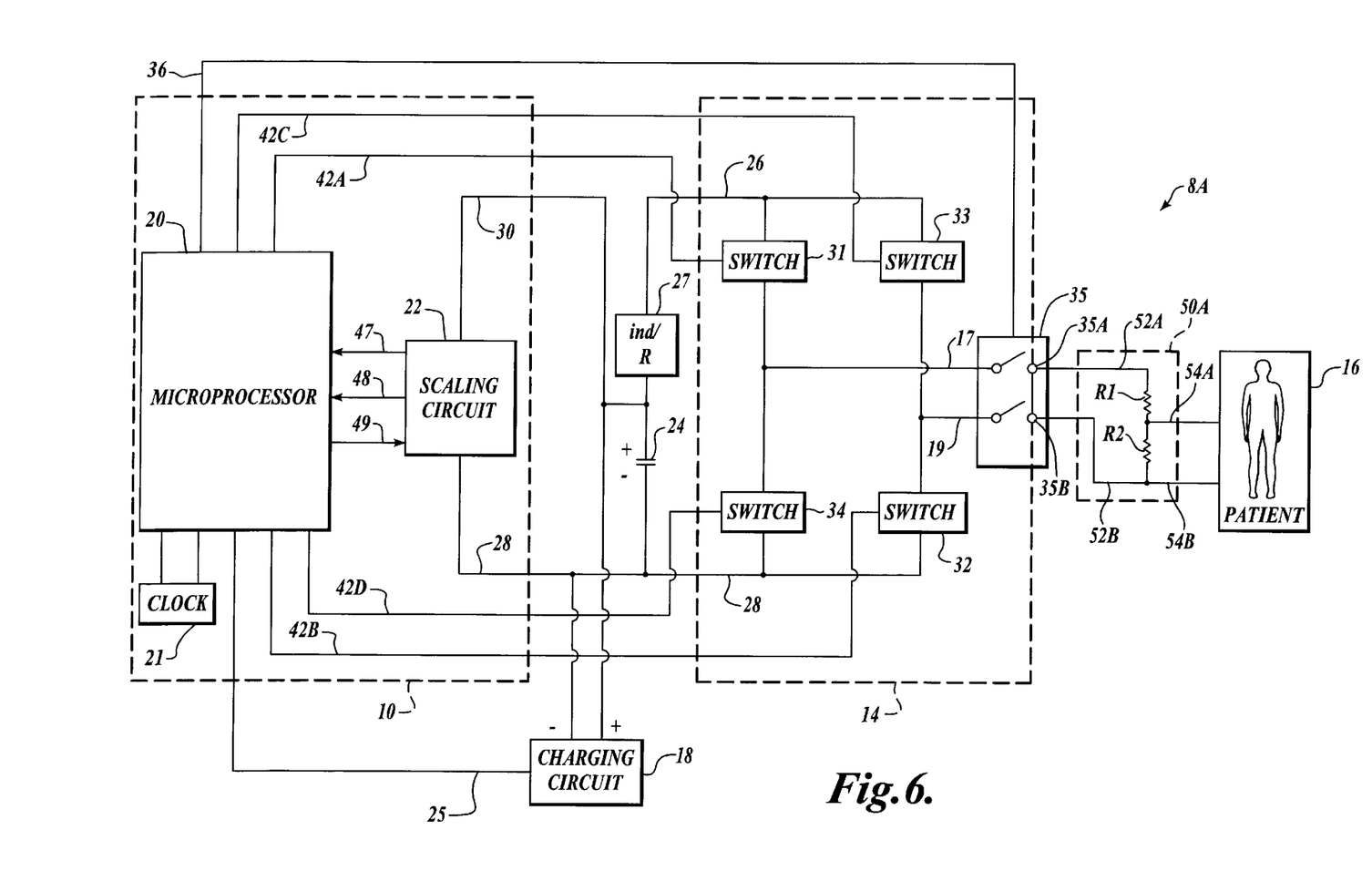
FIG. 6 is a schematic diagram of a biphasic defibrillator coupled to a patient through the energy adjusting circuit of FIG. 2.

FIG. 6 is a schematic diagram of a biphasic defibrillation and energy control circuitry 8A, that is coupled through the energy adjusting circuit 50A to the patient 16. The biphasic circuitry 8A is described in more detail in commonly assigned U.S. Pat. No. 5,924,017, to Sullivan et al., which is hereby incorporated by reference. As will be described in more detail below, the operation of the biphasic circuitry 8A in conjunction with the energy adjusting circuit 50A illustrates that the energy adjusting circuit 50A functions effectively regardless of the polarity of the energy flow through the output ports 35A and 35B.

In order to illustrate the operation of the biphasic circuitry 8A, a brief description of the circuitry is provided. The biphasic circuitry 8A includes a microprocessor 20 that is connected to a charging circuit 18 for charging an energy storage capacitor 24. During the operation of the defibrillator, the microprocessor 20 controls the charging circuit 18 by a signal on a control line 25 to charge the energy storage capacitor 24 to a desired voltage level. To monitor the charging process, the microprocessor 20 is connected to a scaling circuit 22 by a pair of measurement lines 47 and 48, and by a control line 49. The scaling circuit 22 is connected to the energy storage capacitor 24 by a bridge line 28, which connects to the negative lead of the capacitor, and by a line 30, which connects to the positive lead of the capacitor. A clock 21 is also connected to the microprocessor 20.

The scaling circuit 22 is used to step down the voltage across the energy storage capacitor 24 to a range that may be monitored by the microprocessor 20. The energy storage capacitor 24 can be charged to a range of voltage levels, with the selected level depending on the patient and other parameters. Preferably, the size of the energy storage capacitor falls within a range from 150 uF to 200 uF. In order to generate the necessary defibrillation pulse for external application to a patient, the energy storage capacitor is charged to between 100 volts and 2,200 volts. To detect small percentage changes in the selected voltage level of the energy storage capacitor 24, the scaling circuit 22 is adjustable to measure different voltage ranges. The adjusted output is measured by the microprocessor 20 on measurement line 48.

After charging to a desired level, the energy stored in the energy storage capacitor 24 may be delivered to the patient 16 in the form of a defibrillation pulse. An output circuit 14 is provided to allow the controlled transfer of energy from the energy storage capacitor to the patient. The output circuit 14 includes four switches 31, 32, 33, and 34, each switch on a leg of the output circuit arrayed in the form of an "H" (hereinafter the "H-bridge" output circuit). Switch 32 may be implemented as an IGBT switch or pair of IGBT switches, while switches 31, 33, and 34 may be SCRs. Switches 31 and 33 are coupled through a protective component 27 to the positive lead of the energy storage capacitor 24 by a bridge line 26. The protective component 27 limits the current and voltage changes from the energy storage capacitor 24, and has both inductive and resistive properties. Switches 32 and 34 are coupled to the energy storage capacitor 24 by a bridge line 28.

The patient 16 is connected to the left side of the H-bridge by an apex line 17, and to the right side of the H-bridge by a sternum line 19. As depicted in FIG. 6, the apex line 17 and the sternum line 19 are connected by a patient isolation relay 35 to output ports 35A and 35B, respectively. The microprocessor 20 is connected to the switches 31, 32, 33, and 34 by control lines 42a, 42b, 42c, and 42d, respectively, and to the patient isolation relay 35 by control line 36. Application of appropriate control signals by the microprocessor over the control lines causes the switches to be opened and closed, and the output circuit 14 to conduct energy from the energy storage capacitor 24 to the patient.

Defibrillator 8A generates a biphasic defibrillation pulse for application to the patient 16. When the energy storage capacitor 24 is charged to a selected energy level and the patient isolation relay 35 is closed, the switches 31 and 32 are switched on so as to connect the energy storage capacitor with the apex line 17 and sternum line 19 for the application of a first phase of a defibrillation pulse to the patient. The stored energy travels from the positive terminal of the energy storage capacitor 24 on line 26, through switch 31 and apex line 17, across the energy adjusting circuit 50A and patient 16, and back through sternum line 19 and switch 32 to the negative terminal of the capacitor on line 28. The first phase of the biphasic pulse is therefore a positive pulse from the apex to the sternum of the patient. Before the energy storage capacitor 24 is completely discharged, the switch 32 is biased off to prepare for the application of the second phase of the biphasic pulse.

The energy flow through the energy adjusting circuit 50A during the first phase of the biphasic defibrillation pulse is thus similar to the energy flow described above with reference to FIG. 2. In other words, the current travels from apex line 17 through coupling line 52A and through resistor R1, which absorbs part of the energy. The current is then divided between flowing through resistor R2, and through electrode 54A and the patient 16. Thus, part of the remaining energy is absorbed by resistor R2, while part is applied to the patient 16 in the form of the first phase of the biphasic defibrillation pulse. The current then travels through the coupling line 52B to the sternum line 19.

After the end of the first phase of the biphasic defibrillation pulse, switches 33 and 34 are switched on to start the second phase of the biphasic pulse. Switches 33 and 34 provide a path to apply a negative defibrillation pulse to the patient 16. The energy travels from the positive terminal of the energy storage capacitor 24 on line 26, through switch 33 and sternum line 19, across the energy adjusting circuit 50A and the patient 16, and back through apex line 17 and switch 34 to the negative terminal of the energy storage capacitor on line 28. The polarity of the second phase of the defibrillation pulse is therefore opposite in polarity to the first phase of the biphasic pulse. The end of the second phase of the biphasic pulse is truncated by switching on switch 31 to provide a shorted path for the remainder of the capacitor energy through switches 31 and 34. After the second phase is truncated, all four of the switches 31 to 34 are switched off and the patient isolation relay 35 is opened. The energy storage capacitor 24 may then be recharged to prepare the biphasic circuitry 8A to apply another defibrillation pulse.

The energy flow through the energy adjusting circuit 50A during the second phase of the biphasic defibrillation pulse illustrates that the circuit functions effectively regardless of the polarity of the energy flow from the output ports 35A and 35B. More specifically, during the second phase of the biphasic defibrillation pulse, the current flows from the sternum line 19 through coupling line 52B. The current is then divided between the resistor R2, and the electrode 54B and patient 16. Thus, part of the energy is absorbed by the resistor R2, and part of the energy is applied to the patient 16 as the second phase of the biphasic defibrillation pulse. The current then travels through resistor R1 which absorbs another portion of the energy. The current then travels through coupling line 52A to apex line 17. Because of the nature of the resistive network of the energy adjusting circuit 50A, approximately the same proportion of energy is absorbed by the resistors R1 and R2 during the second phase of the biphasic defibrillation pulse as was absorbed during the first phase. Thus, the energy adjusting circuit 50A functions effectively regardless of the polarity of the energy flow from the output ports 35A and 35B.

As an example of how a specific pulse width and tilt can be selected for a specific circuit such as that shown in FIG. 6, in one embodiment the capacitor 24 has a value of 196 uF. In this embodiment, the capacitor can deliver a 7.3 ms first phase pulse width into 50 ohms, resulting in a 67% tilt, or a 9.6 ms pulse width into 100 ohms, giving a 53% tilt. For whatever capacitor value is selected, the impedance of the energy adjusting circuit 50A can be selected to give the best pulse width and tilt available.

While the preferred embodiment of the invention has been illustrated and described, it will be appreciated that various changes can be made therein without departing from the spirit and scope of the invention. For example, while the energy adjusting circuit has generally been shown as being external to the defibrillator, it could be incorporated into the circuitry of the defibrillator. In one such incorporated embodiment, an appropriate switching mechanism could be used to couple the energy adjusting circuit into and out of the circuit path of the defibrillation energy flow, depending on whether regular or low energy defibrillation levels were desired.

The embodiments of the invention in which an exclusive property or privilege is claimed are defined as follows:

1. An energy adjusting circuit for use with a biphasic defibrillator, the defibrillator having an output with a circuit path for applying defibrillation pulse energy to a patient, the energy adjusting circuit comprising:
   an energy absorbing component for absorbing energy while the defibrillator is applying defibrillation pulse energy to the patient, the energy absorbing component when coupled in the circuit path of the output of the defibrillator comprising:
      a first energy absorbing element coupled between a first output of the defibrillator and a first circuit node;
      a second energy absorbing element coupled between a second output of the defibrillator and a second circuit node; and
      a third energy absorbing element coupled between the first and second circuit nodes; and
   a coupling component for coupling the energy absorbing component in the circuit path of the output of the defibrillator, the energy absorbing component when coupled in the circuit path of the output of the defibrillator absorbing a majority of the energy from the defibrillator while the defibrillator is applying defibrillation pulse energy to the patient.

2. The energy adjusting circuit of claim 1, wherein the components of the energy adjusting circuit are formed from only passive elements, such that active switching is not performed within the energy adjusting circuit during normal defibrillator operation.

3. The energy adjusting circuit of claim 1, wherein the defibrillator further comprises an output port and the coupling component comprises a plug for plugging into the output port of the defibrillator.

4. The energy adjusting circuit of claim 1, wherein the coupling component comprises a switch, the switch coupling the energy absorbing component into the circuit path of the output of the defibrillator.

5. The energy adjusting circuit of claim 1, further comprising an impedance adjuster, the impedance adjuster adjusting the impedance of the energy adjusting circuit so as to alter the amount of defibrillation pulse energy that is reduced.

6. The energy adjusting circuit of claim 1, wherein the defibrillator has at least first and second energy settings for applying first and second levels of defibrillation pulse energy to a patient.

7. The energy adjusting circuit of claim 1, wherein the energy adjusting circuit is able to reduce the defibrillation pulse energy that is applied to the patient to approximately 0.2 joules or less.

8. The energy adjusting circuit of claim 1, wherein the energy adjusting circuit reduces the defibrillation pulse energy that is applied to the patient by a factor of approximately 10 or more.

9. The energy adjusting circuit of claim 1, further comprising an indicator circuit, the indicator circuit being coupled to the defibrillator and providing an indication of when the energy absorbing component is coupled in the circuit path of the output of the defibrillator.

10. The energy adjusting circuit of claim 9, wherein the indicator circuit further provides an indication of the reduced energy settings of the defibrillator that result when the energy absorbing component is coupled in the circuit path of the output of the defibrillator.

11. The energy adjusting circuit of claim 1, wherein the energy absorbing component has a selected impedance so as to cause the defibrillation pulse energy waveform that is output from the defibrillator to have a selected pulse width and tilt.

12. The energy adjusting circuit of claim 11, wherein the selected impedance of the energy absorbing component is significantly greater than an expected maximum patient impedance such that varying patient impedances below the expected maximum does not significantly affect the pulse width or tilt.

13. The energy adjusting circuit of claim 1, wherein the first and third energy absorbing elements comprise two resistive components coupled together to form an energy divider.

14. The energy adjusting circuit of claim 13, wherein the energy adjusting circuit further comprises two electrodes, the third energy absorbing element being coupled between the two electrodes.

15. The energy adjusting circuit of claim 14, wherein the second energy absorbing element comprises a third resistive component.

16. The energy adjusting circuit of claim 13, further comprising an isolation network coupled in series with one of the two resistive components.

17. The energy adjusting circuit of claim 16, wherein the isolation network comprises two diodes, each coupled anode-to cathode.

18. An energy adjusting circuit for use with a biphasic defibrillator, the defibrillator comprising first and second output nodes, the energy adjusting circuit comprising:
   first and second circuit nodes;
   a first energy reducing component coupled between said first output node and said first circuit node;
   a second energy reducing component coupled between said second output node and said second circuit node;
   a third energy reducing component coupled between said first and second circuit nodes;
   a first electrode coupled to the first circuit node; and
   a second electrode coupled to the second circuit node.

19. The energy adjusting circuit of claim 18, wherein the first, second and third energy reducing components are selected to have impedances such that a waveform that is output from the defibrillator will have a selected pulse width and tilt.

20. The energy adjusting circuit of claim 18, wherein the impedances of the first, second and third energy reducing components are selected so as to be able to absorb a majority of the energy that is output by the defibrillator.

21. The energy adjusting circuit of claim 18, wherein the impedance of the energy adjusting circuit is made to be adjustable.

22. The energy adjusting circuit of claim 18, further comprising an indicator circuit, the indicator circuit providing an indication of when the energy adjusting circuit is coupled to the first and second output nodes of the defibrillator.

23. An energy adjusting circuit for use with a defibrillator that applies defibrillation pulses to a patient in the form of a waveform with a width and tilt, the tilt of the waveform produced by the defibrillator without the energy adjusting circuit being variable, the energy adjusting circuit comprising:

an energy reducing component that reduces part of the defibrillation pulse energy that is applied to the patient, the tilt of the waveform that is applied to the patient being determined in part by the impedance of the energy reducing component, the value of the impedance of the energy reducing component being selected so as to produce a predetermined tilt in the waveform, the predetermined tilt varying less than a selected amount over a selected range of patient impedances.

24. The energy adjusting circuit of claim 23, wherein the impedance of the energy reducing component absorbs the majority of the energy that is output from the defibrillator.

25. The energy adjusting circuit of claim 23, further comprising an indicator circuit, the indicator circuit providing an indication of the reduced energy level settings for the defibrillator that are determined by the impedance of the energy reducing component.

26. The energy adjusting circuit of claim 23, wherein the defibrillator has at least first and second energy settings for applying first and second levels of defibrillation pulse energy to a patient.

27. The energy adjusting circuit of claim 23, wherein the energy adjusting circuit is able to reduce the defibrillation pulse energy that is applied to the patient to approximately 0.2 joules or less.

28. The energy adjusting circuit of claim 23, wherein the energy absorbing component comprises two resistive components coupled together to form an energy divider.

29. The energy adjusting circuit of claim 25, wherein the energy adjusting circuit reduces the defibrillation pulse energy that is applied to the patient by a factor of approximately 10 or more.

30. The energy adjusting circuit of claim 28, wherein the energy adjusting circuit further comprises two electrodes, one of the electrodes being coupled to the output of the defibrillator, and the other electrode being coupled to a circuit node between the two resistive components.

31. In a defibrillator for applying defibrillation pulse energy to a patient, the defibrillator including defibrillation energy and control circuitry, the improvement comprising:

an energy adjusting circuit, the energy adjusting circuit comprising a coupling component for coupling the energy adjusting circuit to the defibrillation energy and control circuitry, the defibrillator and control circuitry when not coupled to the energy adjusting circuit producing a defibrillation waveform with a variable pulse width and tilt, the energy adjusting circuit when coupled to the defibrillation and control circuitry adjusting the shape of the defibrillation waveform that is applied to the patient such that the resulting defibrillation waveform has an approximately fixed pulse width and tilt over a selected range of patient impedances.

32. The improvement of claim 31, wherein the energy adjusting circuit comprises a divider circuit.

33. The improvement of claim 31, wherein the defibrillator further comprises an output port and the coupling component comprises a plug for plugging into the output port of the defibrillator.

34. The improvement of claim 31, wherein the coupling component comprises a switch, the switch selectively coupling the energy adjusting circuit to the defibrillation energy and control circuitry.

35. An energy adjusting circuit for use with a defibrillator, the defibrillator having an output with a circuit path for applying defibrillation pulse energy to a patient through a pair of electrodes, the energy adjusting circuit comprising:

an energy adjusting component for absorbing part of the defibrillation pulse energy from the defibrillator;

a coupling component for coupling the energy adjusting component in the circuit path of the output of the defibrillator;

the defibrillator being couplable to the patient through the electrodes without the energy adjusting component being coupled in the circuit path of the output of the defibrillator, the defibrillator without the energy adjusting component in the circuit path applying defibrillation pulse energy to the patient in a waveform with a variable pulse width and a variable tilt; and the energy adjusting component when coupled in the circuit path of the output of the defibrillator reducing the defibrillation pulse energy to a level that is lower than the defibrillation pulse energy that would have been applied to the patient if the energy adjusting component had not been coupled in the circuit path of the output of the defibrillator, and resulting in a waveform with a relatively fixed pulse width and fixed tilt.

36. The energy adjusting circuit of claim 35, wherein the energy adjusting component comprises a resistive component for absorbing part of the defibrillation pulse energy.

* * * * *